United States Patent [19]

Tsao et al.

[11] 4,134,926
[45] Jan. 16, 1979

[54] PRODUCTION OF ETHYLENE FROM ETHANOL

[75] Inventors: Utah Tsao, Jersey City; Howard B. Zasloff, Rockaway, both of N.J.

[73] Assignee: The Lummus Company, Bloomfield, N.J.

[21] Appl. No.: 788,304

[22] Filed: Apr. 18, 1977

[51] Int. Cl.$^2$ .............................................. C07C 1/24
[52] U.S. Cl. ..................................................... 260/682
[58] Field of Search ........................................ 260/682

[56] References Cited

U.S. PATENT DOCUMENTS

| | | | |
|---|---|---|---|
| 2,378,236 | 6/1945 | Miller | 260/682 |
| 3,915,893 | 10/1975 | Flanigan et al. | 260/682 |
| 3,979,472 | 9/1976 | Butter | 260/682 |

*Primary Examiner*—C. Davis
*Attorney, Agent, or Firm*—Marn & Jangarathis

[57] ABSTRACT

Ethanol is dehydrated to ethylene at dehydration reaction conditions in the presence of a dehydration catalyst, with the reaction being effected in a fluidized bed of the dehydration catalyst. The use of a fluidized bed has been found to improve overall yields, with it being possible to achieve yields of 99+%.

4 Claims, 1 Drawing Figure

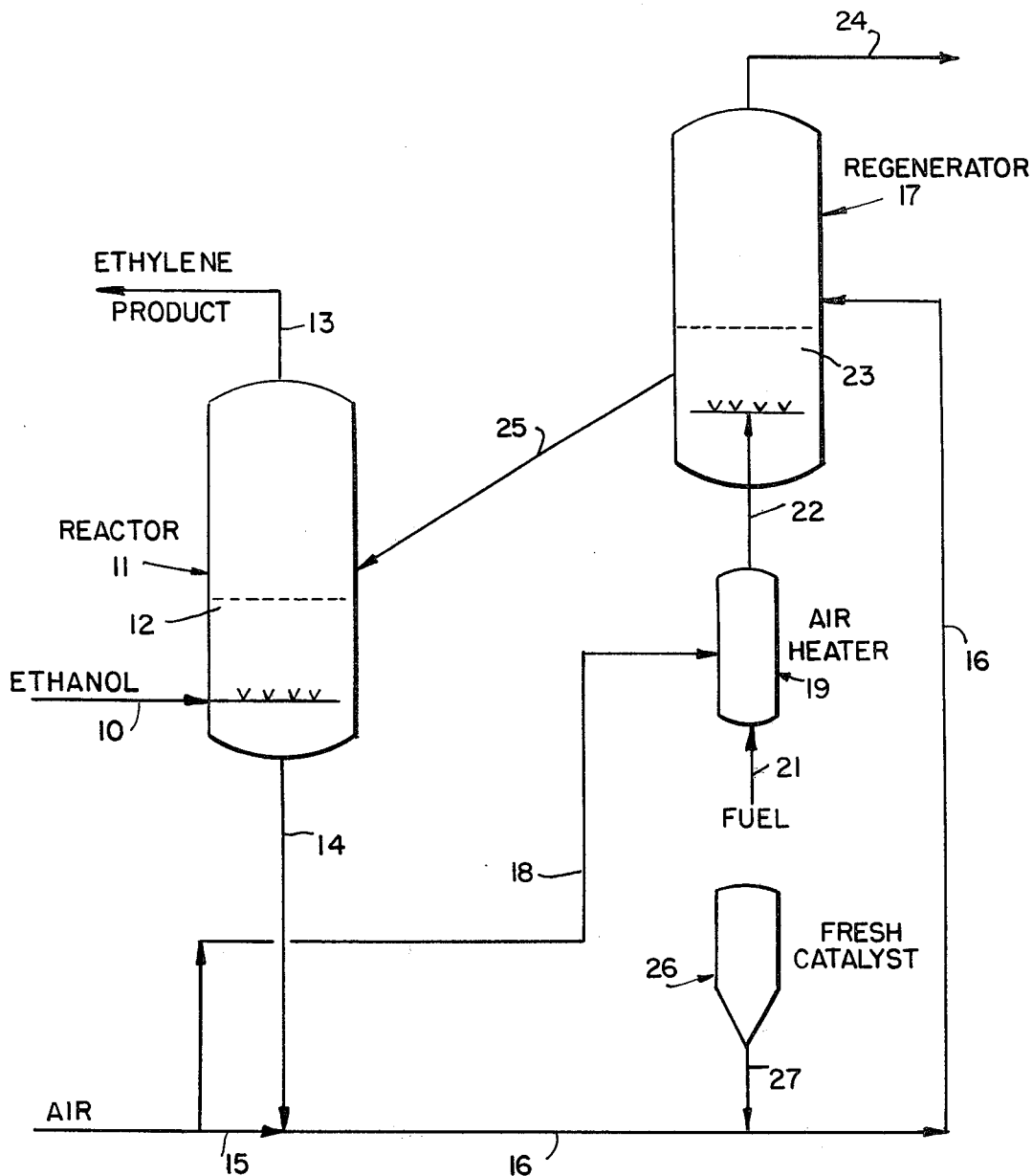

PRODUCTION OF ETHYLENE FROM ETHANOL

This invention relates to the production of ethylene, and more particularly to a new and improved process for converting ethanol to ethylene.

In the conventional process of converting ethanol to ethylene, such conversion is effected in a reactor containing long parallel vertical tubes packed with a dehydration catalyst, such as alumina. Since the reaction is endothermic, such tubes are heated externally be a heat transfer medium, such as Dowtherm. In general, in such a conventional process the yields do not exceed about 95°.

An object of the present invention is to provide a new and improved process for producing ethylene from ethanol.

A further object of the present invention is to produce ethylene from ethanol at improved yields.

These and other objects of the present invention should be more readily apparent from reading the following detailed description thereof.

In accordance with the present invention, ethanol is converted to ethylene by contacting the ethanol with a dehydration catalyst at dehydration conditions in a fluidized bed reactor in which the catalyst is maintained in a fluidized state. It has been found that by using a fluidized bed reactor, it is possible to achieve ethylene yields of at least 99%.

The dehydration of ethanol to ethylene in the fluidized bed reactor is generally effected at a temperature and residence time to provide an ethanol conversion of at least 99%. The fluidized bed reactor temperature is generally at least 700° F, with the best results being obtained at temperature of at least 750° F. The reactor is generally not maintained at a temperature of above 1000° F in that although the use of higher temperatures is possible, no additional beneficial results are generally achieved by the use of such higher temperatures. Most generally, the temperature does not exceed 900° F.

The residence time for the reaction is selected to achieve the desired conversion at the reaction temperature. As hereinabove noted, such a conversion is generally at least 99%, based on ethanol. The residence time is in general at least 1 second. Residence times longer than those required to achieve the desired conversion could be employed; however, no additional beneficial result is usually obtained by the use of such longer residence times. As known in the art, the residence time can be controlled by controlling the height of the fluidized bed. At the preferred reaction temperature of at least 750° F, the residence time is generally in the order of from 1 to 10 seconds.

The catalyst employed in the bed may be any one of wide variety of dehydration catalysts. Such catalysts are generally known in the art, and no details in this respect are deemed necessary for a complete understanding of the present invention. Such catalysts are generally also cracking catalysts. As illustrative dehydration catalysts, there may be mentioned: alumina, silica-alumina, activated clays, zeolites, etc. A preferred catalyst is a silica-alumina cracking catalyst as a result of its ready availability.

The dehydration catalyst must be periodically regenerated to remove carbon and tars. In accordance with the present invention, the regeneration can be effected in a continuoous manner without shutting down of the reactor by passing catlyst from the fluidized bed dehydration reactor to a regeneration reactor wherein the carbon and tar can be burned off of the catalyst. In addition, the endothermic heat requirements for the dehydration reaction can be provided by the circulating catalyst, which is heated by the hot gas in the regenerator. It is to be understood, however, that the endothermic requirements could be provided in another manner.

The invention will be further described with respect to an embodiment thereof illustrated in the accompanying drawing wherein:

The drawing is a simplified schematic flow diagram of an embodiment of the present invention.

Referring now to the drawing, vaporized ethanol in line 10 is introduced into a fluidized bed reactor, schematically generally indicated as 11. The reactor 11 contains a suitable dehydration catalyst, and the catalyst bed 12 is maintained in a fluidized state by the gaseous ethanol introduced through line 10. As known in the art, the ethanol is introduced at a superficial velocity sufficient to maintain the catalyst bed 12 in a fluidized state, with such superficial velocity generally being in the order of from about 0.25 foot per second to about 3 feet per second.

The fluidized bed reactor 11 is maintained at dehydration reaction conditions, as hereinabove described, to effect dehydration of the ethanol to ethylene. Ethylene product, including water, as co-reaction product, is withdrawn from the fluidized bed reactor 11 through line 13.

A portion of the catalyst in fluidized bed reactor 11 is withdrawn through line 14 and transported by air line 15 through line 16, and introduced into a regenerator reactor, schematically indicated as 17. Another portion of air in line 18 is introduced into an air heater 19 wherein the air is heated by a suitable fuel, introduced through line 21. The heater air withdrawn from air heater 19 through line 22 is introduced into the regenerator 17.

The regenerator 17 is preferably operated as a fluid bed reactor wherein the catalyst is maintained as a fluidized bed, indicated as 23. The bed 23 is maintained in a fluidized state by the heated air introduced through line 22.

The regenerator is operated at a temperature to effect heating of the catalyst, whereby heated catalyst, can be withdrawn from regenerator 17 for introduction into the dehydration reactor 11 to provide the heat requirements for the endothermic dehydration reaction. In addition, the heating in reactor 17 effects regeneration of the catalyst by removing carbon and tar therefrom.

The combustion by-products, as well as air, is withdrawn from regenerator reactor 17 through line 24.

The heated catalyst is withdrawn from regenerator 17 through line 25 and introduced into the reactor 11.

Fresh catalyst for the system is maintained in a fresh catalyst hopper 26, and such fresh catalyst can be provided through the regenerator 17 by passing catalyst from the hopper 26 through line 27 for combination with the catalyst in line 16.

The invention will be further described with respect to the following example; however, the scope of the present invention is not to be limited thereby:

EXAMPLE

Vaporized ethanol was introduced into a jacketed fluidized bed reactor at a temperature of 750° F, with the fluidized bed of silica-alumina cracking catalyst being maintained at a temperature of 750° F by circulating molten salt through the jacket of the reactor. The ethanol was introduced at a log-mean average superficial velocity of 0.74 feet per second. The residence time of the reaction was 2.7 seconds and the reactor pressure was 9.6 psig. The run was conducted at steady state for 123 minutes. The ethanol conversion was 99.6%, the percent selectivity to ethylene was 99.9% and the percent yield of ethylene was 99.5%. The reactor effluent had the following composition: water, 50.02%; ethylene, 49.75%; acetaldehyde, 0.04%; ethanol, 0.19%, all mole percent.

The present invention is particularly advantageous in that it is possible to effect dehydration of ethanol to ethylene at yields of 99% and better. The marked increase in yield which resulted from the use of a fluidized bed reactor, instead of a fixed bed reactor, was completely unexpected.

Numerous modifications and variations of the present invention are possible in light of the above teachings and, therefore, within the scope of the appended claims the invention may be practiced otherwise than as particularly described.

What is claimed is:

1. A process for producing ethylene from ethanol, comprising:
   introducing ethanol into a reactor containing a dehydrating catalyst for dehydrating ethanol to ethylene, said ethanol maintaining said catalyst in a fluidized state in said reactor, said reactor being maintained at a temperature of at least 700° F;
   withdrawing an ethylene containing effluent from the reactor;
   withdrawing a portion of the catalyst from the reactor;
   introducing withdrawn catalyst into a regenerator wherein the catalyst is heated in a fluidized state by heated gas, said heating effecting regeneration of the catalyst; and
   recycling heated catalyst from the regenerator to the reactor, said heated catalyst providing heat requirements for dehydration of ethanol to ethylene.

2. The process of claim 1 wherein ethanol is converted in said reactor at a conversion of at least 99% to provide ethylene in a yield of at least 99%.

3. The process of claim 2 wherein the catalyst is selected from the group consisting of alumina, silica-alumina, activated clays and zeolites.

4. The process of claim 3 wherein the catalyst is silica-alumina cracking catalyst.

* * * * *